United States Patent [19]

Noda

[11] Patent Number: 5,071,412
[45] Date of Patent: Dec. 10, 1991

[54] DEVICE AND METHOD FOR PERFORMING CHOLANGIOGRAPHY

[75] Inventor: Wayne A. Noda, Mission Viejo, Calif.

[73] Assignee: Laparomed Corporation, Irvine, Calif.

[21] Appl. No.: 663,498

[22] Filed: Mar. 1, 1991

[51] Int. Cl.⁵ .............................................. A61M 5/00
[52] U.S. Cl. ..................................... 604/268; 604/52; 604/176
[58] Field of Search ............... 604/268, 115, 176, 174, 604/35, 52, 51

[56] References Cited

U.S. PATENT DOCUMENTS

| | | | |
|---|---|---|---|
| 3,685,509 | 8/1972 | Beutall | 604/115 |
| 3,918,456 | 11/1975 | Patel . | |
| 4,044,757 | 8/1977 | McWhorter et al. . | |
| 4,044,758 | 8/1977 | Patel . | |
| 4,306,566 | 12/1981 | Sinko . | |
| 4,393,870 | 7/1983 | Wagner | 604/115 |
| 4,536,180 | 8/1985 | Johnson | 604/268 |
| 4,547,187 | 10/1985 | Kelly . | |
| 4,573,970 | 3/1986 | Wagner | 604/115 |
| 4,662,367 | 5/1987 | Gore, Jr. | 604/268 |
| 4,689,040 | 8/1987 | Thompson | 604/268 |
| 4,747,823 | 5/1988 | Buchanan . | |
| 4,792,330 | 12/1988 | Lazarus et al. . | |
| 4,817,604 | 4/1989 | Smith, III . | |
| 4,935,006 | 6/1990 | Hasson | 604/268 |

*Primary Examiner*—Paul J. Hirsch
*Attorney, Agent, or Firm*—Townsend and Townsend

[57] ABSTRACT

A device for introducing fluids into the lumen of a body duct comprises an elongate shaft having a mechanism at its distal end for capturing the duct. A needle is disposed within an axial passage in the shaft, and a mechanism for reciprocating the needle is located at the proximal end of the shaft. In this way, the duct can be captured with the capture mechanism and pierced with the needle. The fluid is then provided to the lumen of the duct through a perfusion port located at or near the distal end of the needle. Optionally, a mechanism for applying a vacuum externally to the duct within the capture mechanism is provided to help hold the duct and open the interior to facilitate introduction of the fluid.

21 Claims, 4 Drawing Sheets

DEVICE AND METHOD FOR PERFORMING CHOLANGIOGRAPHY

BACKGROUND OF THE INVENTION

1. Field of the Invention

The present invention relates generally to the structure and use of surgical instruments. More particularly, the present invention relates to a device and method for introducing a fluid, such as contrast medium, to a body duct, such as the cystic duct.

Cholangiography is a procedure for the X-ray of a patient's bile duct which is commonly performed to locate duct stones during surgical gallbladder removal. The presence of gallstones in the biliary ducts, particularly the common bile duct, is a painful and potentially fatal condition which exists in a significant percentage of patients who have undergone gallbladder removal. Surgical exploration of the common bile duct, however, is itself a relatively risky procedure which is associated with significant morbidity. Thus, the ability to locate the presence of gallstones by cholangiography is of significant benefit to the patient.

Surgical gallbladder removal, referred to as cholecystectomy, is most commonly performed as an open surgical procedure through a major incision in the patient's abdomen. After the gallbladder is removed, and the cystic duct ligated, a flexible catheter is introduced through a small incision in either the cystic duct or the common bile duct. A suitable contrast medium may then be introduced through the catheter to permit X-ray detection of any gallstones which may be present in the ducts.

Laparoscopic surgical removal of the gallbladder is becoming increasingly popular. Laparoscopic surgery is performed through small incisions in the patient's abdomen allowing the necessary surgical instruments to be introduced through a tube, such as a cannula, while the physician observes manipulation of the instruments through a laparoscope. Such laparoscopic surgery offers significant advantages over conventional "open" cholecystectomy. In particular, the laparoscopic cholecystectomy is usually less traumatic, requires a shorter recovery time, and is significantly less costly than the corresponding open surgical procedure.

The performance of cholangiographic detection of gallstones in the bile ducts following a laparoscopic cholecystectomy, however, is problematic. Access to the cystic duct and the common bile duct is necessarily more limited than in the open surgical procedure, and the introduction of a catheter to either of the ducts is difficult to achieve. While the use of a catheter and syringe for introducing contrast medium is possible, it is difficult to access, introduce, and seal the penetration to achieve effective cholangiography.

For these reasons, it would be desirable to provide improved devices and methods to facilitate the introduction of fluids, such as contrast media, to body ducts, such as the biliary ducts. It would be particularly desirable to provide a single instrument having the combined capabilities of capturing and immobilizing the target duct as well as penetrating a wall of the duct to introduce the fluid into the duct lumen. Such devices should be easy to manipulate, preferably allowing all manipulations to be performed with a single hand, and should be suitable for laparoscopic and other "least invasive surgical" procedures. The device and method of the present invention should further assure that the fluid is introduced accurately within the duct lumen and that the fluid is able to be transported to other regions of the duct system. The device should also cause minimum damage to the duct which is being treated.

2. Description of the Background Art

Catheters and cannulas for introducing contrast media to a patient's bile ducts following open surgical gall bladder removal are described in the patent and medical literature. See, for example, U.S. Pat. Nos. 4,747,823; 4,547,187; 4,306,566; 4,044,757; 4,044,758; and 3,918,456. Devices for clamping the cystic duct in conjunction with the open surgical introduction of a cholangiogram catheter are described in U.S. Pat. Nos. 4,817,604 and 4,792,330.

SUMMARY OF THE INVENTION

The present invention provides improved devices and methods for introducing fluids to the lumen of a body duct. The invention combines the ability to capture the duct, pierce the duct with a needle, and deliver a desired fluid through the needle to the duct lumen in a single device. The design of the device assures proper alignment of a perfusion port on the needle with the lumen so that fluid is accurately delivered to the duct. Moreover, by virtue of the clamping action by the device on the duct, leakage of fluid through the needle penetration is minimized. The device is easy to use and can for the most part be manipulated with one hand. Use of the device results in minimal injury to the duct and is particularly suitable in laparoscopic and other least invasive surgical procedures.

The device of the present invention includes a shaft having means at its distal end for capturing the duct and means at its proximal end for reciprocating a needle within the shaft to puncture the duct while it is held by the distal end of the shaft. Usually, the needle reciprocating means is "spring-loaded" so that it can be operated by a simple release mechanism, facilitating its use by the treating physician. Moreover, the travel of the needle relative to the captured duct is carefully calibrated (optionally being adjustably calibrated) so that the fluid perfusion port on the needle necessarily comes to rest within the lumen of the duct. Optionally, vacuum means are provided as part of the capture means on the shaft to expand the body duct and further assure free flow of fluid from the perfusion port into the lumen and the remainder of the duct system.

According to the method of the present invention, the body duct, usually the cystic duct, is first captured by the distal end of the device shaft. After optionally opening the lumen with an external applied vacuum, the retracted needle is advanced to pierce through a wall surface of the duct so that the perfusion port lies within the duct lumen. The fluid, for example, contrast medium, is then introduced from the proximal end of the needle and out through the perfusion port into the duct lumen. The method of the present invention is advantageously employed as part of a laparoscopic procedure for removing the gallbladder where, after cystic duct ligation, the device is manipulated through a cannula to introduce contrast media to the biliary ducts to facilitate performing a cholangiogram procedure. Another advantage is that the anatomy is visualized for proper identification of ducts and arteries.

DESCRIPTION OF THE SPECIFIC EMBODIMENTS

Figure 1:
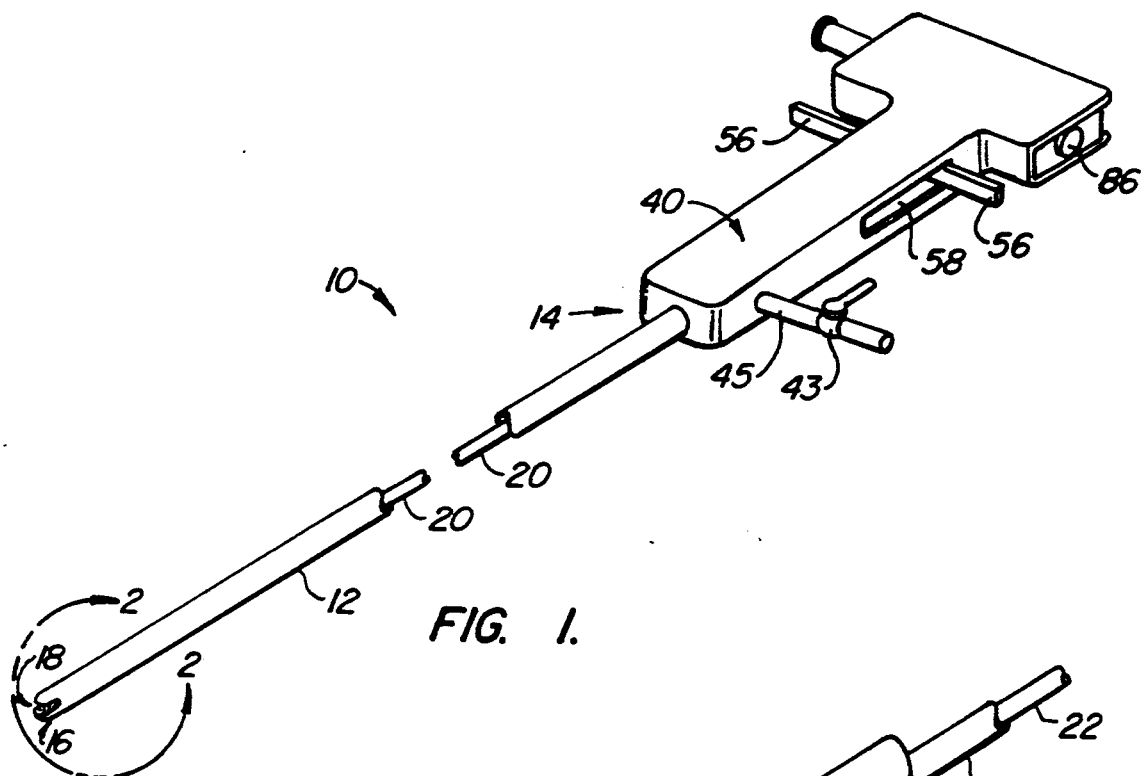
FIG. 1 is a perspective view of a fluid-introducing device constructed in accordance with the principles of the present invention.

The device and method of the present invention are useful for introducing fluids, such as contrast media, to a variety of body ducts, such as the cystic duct, bile duct, pancreatic duct, hepatic duct, uterine tube, ureter, blood vessels, and the like. The present invention is particularly useful for introducing contrast media as part of performing an X-ray imaging procedure, such as a cholangiogram, arteriograph, veinograph, ureterography, pancreatograph, and the like. While any of these procedures might be performed in conjunction with open surgery, the present invention will find its greatest use in the performance of laparoscopic, arthroscopic, and endoscopic procedures, where the device is introduced and manipulated through relatively narrow cannulas, typically having diameters of ten millimeters or less, usually five millimeters or less. The device and method of the present invention will find perhaps their greatest use in performing cholangiograms in conjunction with laparoscopic gallbladder removal procedures.

The device of the present invention comprises an elongate shaft having proximal and distal ends. The elongate shaft will usually have a circular cross-section, more usually comprising a cylindrical tube having an axial passage extending from the proximal to distal end. The dimensions of the shaft are not critical, but the diameter will usually be sufficiently small to allow for passage through a conventional cannula, usually being in the range from about 10 millimeters to five millimeters or less, in diameter. The length of the shaft will be sufficient to permit the distal end to reach any desired location in the body with the proximal end remaining external to the body, typically having a length in the range from about 10 centimeters to 15 centimeters. The shaft will typically be rigid, more typically being formed from a rigid metal or plastic material. Preferably, the shaft will be formed from metal, more preferably from a metal which has an anti-reflective coating.

Means for capturing and securing the body duct will be formed at or mounted on the distal end of the elongate shaft. In the exemplary embodiments, the capture means will comprise an axially or transversely oriented aperture or slot formed within the body of the shaft. The aperture or slot can be used to hook or otherwise grasp the body duct, with a vacuum being optionally applied to hold the duct in place and open the duct lumen. Alternatively, separate hooks, jaws, or other implements, may be provided at or near the distal end of the shaft to engage the duct and optionally open the lumen of the duct using an externally applied vacuum. In all embodiments, the capture means will hold the body duct in a predetermined position, typically transverse to the axis of the shaft, so that the duct can be cleanly pierced by a fluid-delivery needle, as will now be described.

The fluid-delivery needle will be operatively connected to the shaft and will have a sharpened distal end that can penetrate the body duct as the needle is thrust forward. The needle will have a beveled, pencil point, or otherwise sharpened distal end to facilitate the penetration. Usually, the needle will be hollow along its entire length so that the delivered fluid may be introduced at its proximal end. Alternatively, a separate delivery tube or structure could be provided in parallel with at least a proximal portion of the needle. The diameter of the needle will be selected to be compatible with its intended use. The diameter may vary from about 0.6 millimeters to 1.3 millimeters, typically being in the range from about 0.8 millimeters to 1.1 millimeters for use in cholangiographic procedures.

The needle will include at least one perfusion port at or near its distal end for releasing the fluid within the duct lumen. Conveniently, the port may be at the sharpened distal tip. Alternatively, the port may open laterally from one or more sides of the needle so that the fluid is delivered from a point spaced proximally from the distal tip. In either case, the perfusion port will be fluidly connected to the hollow needle lumen (or separate delivery tube) to receive and release the fluid therefrom.

Conveniently, the needle will be mounted to reciprocate within the axial passage of the elongate shaft, and means will be provided to cause reciprocation of the needle relative to the shaft. Conveniently, the reciprocating means will include a spring mechanism that allows the needle to be retracted in the proximal direction and thereafter released by spring action to travel in the distal direction. The spring will both provide the force necessary to cause the needle to pierce the body duct as well as holding the needle in the extended configuration while the fluid is being delivered. After fluid delivery is complete, the needle can be manually retracted to facilitate withdrawal of the device. Optionally, the reciprocating mechanism can be adjustable to permit change of the needle penetration depth within the duct.

Necessary connections will be provided at the proximal end of the device. A fluid connection for connecting the needle to a suitable source of fluid will usually include a flexible tube which allows the needle to reciprocate without changing the fluid connection on the device. Optionally, a vacuum connector is provided for those embodiments having a vacuum-assisted capture means. The vacuum source can be a wall supply, hand pump, motorized pump, or the like. The device will also include a handle or other structure at the proximal end which facilitates manipulation by the treating physician. The handle may be in the form of a pistol grip, a T-grip, or the like. The handle will usually enclose the reciprocating mechanism and may be reusable, requiring only replacement of the needle and shaft assemblies. Usually, however, the entire device will be disposable and stored in sterile packaging.

Referring now to the figures, a number of specific constructions of the devices of the present invention will be described. While each of these constructions may contain features which are particularly useful and which may be preferred aspects of the present invention, it should be appreciated that the specific designs are not meant to be limiting and that the scope of the present invention is more accurately set forth in the preceding paragraphs and in the claims.

Figure 2:
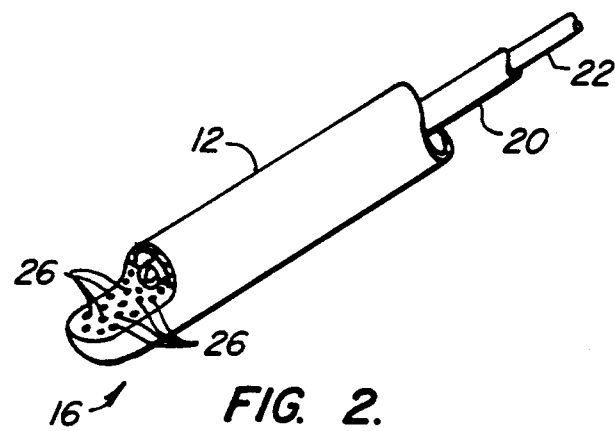
FIG. 2 is a detailed view of the distal end of the device of FIG. 1 illustrating region 2—2.
Figure 3:
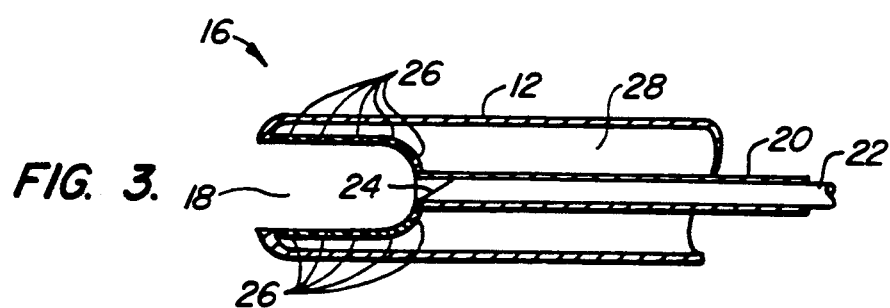
FIG. 3 is a cross-sectional view of the distal end of the device of FIG. 1, shown with the penetration needle in a retracted configuration.
Figure 4:
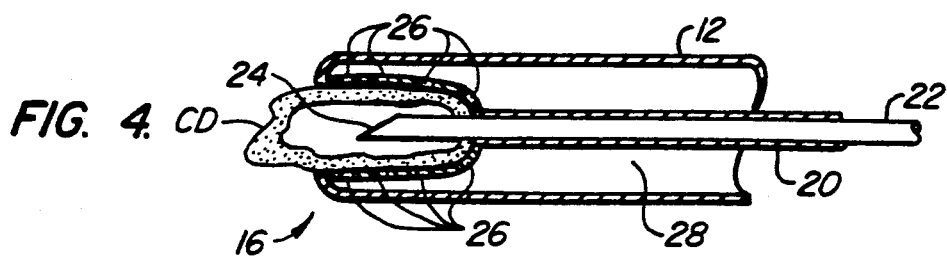
FIG. 4 is a cross-sectional view of the distal end of the device of FIG. 1, shown with the penetration needle in an extended configuration penetrating through a single wall surface of a body duct.

Referring now in particular to FIGS. 1-6, a first embodiment 10 of the device of the present invention will be described. The device 10 includes a shaft 12 having a proximal end 14 and a distal end 16. An aperture 18 for capturing a body duct, such as cystic duct CD (FIG. 4), is formed at the distal end of the shaft, and a needle tube 20 extends from the proximal end 14 (as best observed in FIGS. 5 and 6) to the aperture 18. A fluid-delivery needle 22 is slidably received within the needle tube 20 and can be shifted between a retracted configuration, as illustrated in FIGS. 2 and 3, and an extended configuration, as illustrated in FIG. 4. As best observed in FIG. 4, the needle 22 has a sharpened end 24 which can penetrate a wall of the cystic duct CD when said duct is held in aperture 18.

The aperture 18 includes a plurality of vacuum ports 26, as best illustrated in FIGS. 2-4. The vacuum ports 26 are open to the interior 28 of the shaft 12 so that a vacuum applied to the proximal end of the shaft through vacuum connector 45 (FIGS. 5 and 6) will be directly coupled to the ports in aperture 18. In this way, after the device 10 is manipulated to engage aperture 18 over the exterior of the cystic duct CD, a vacuum may be applied through connector 45 to firmly secure the exterior of the cystic duct CD to the surface of aperture 18. This action further acts to open the interior lumen of the cystic duct CD to facilitate introduction of the contrast media.

For use with the cystic duct CD, the aperture 18 will typically have a width in the transverse direction (i.e., between the opposed faces as observed in FIG. 3) of from about 0.5 millimeters to 2 millimeters and a depth in the axial direction of from about 2 millimeters to 5 millimeters. These dimensions will accommodate most sizes of cystic ducts CD while assuring that the lumen is opened and that the vacuum ports 26 are covered.

Figure 5:
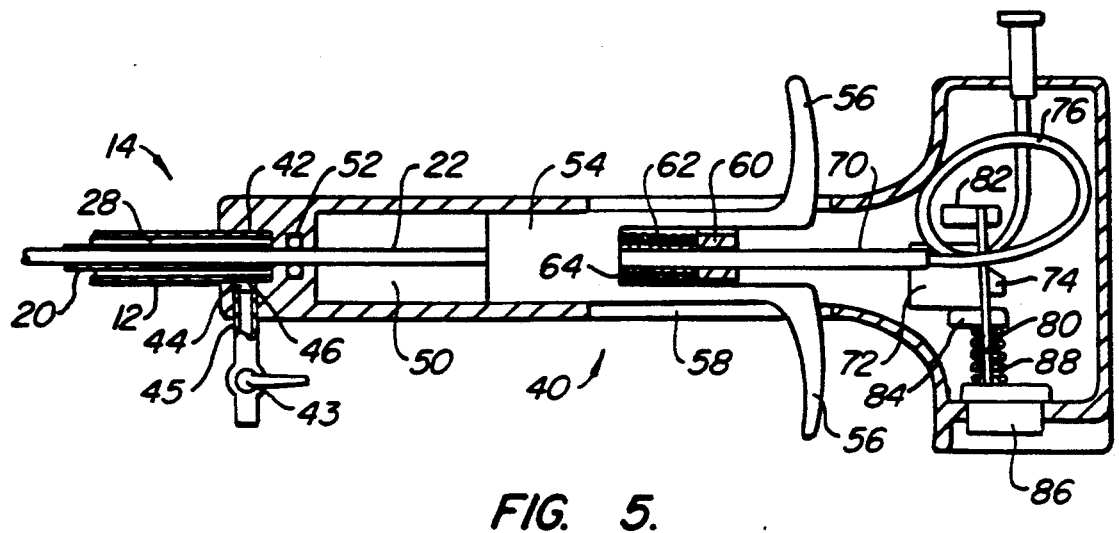
FIG. 5 is a detailed view of the proximal end of the device of FIG. 1, shown in cross-section with the needle reciprocation mechanism in a retracted configuration.
Figure 6:
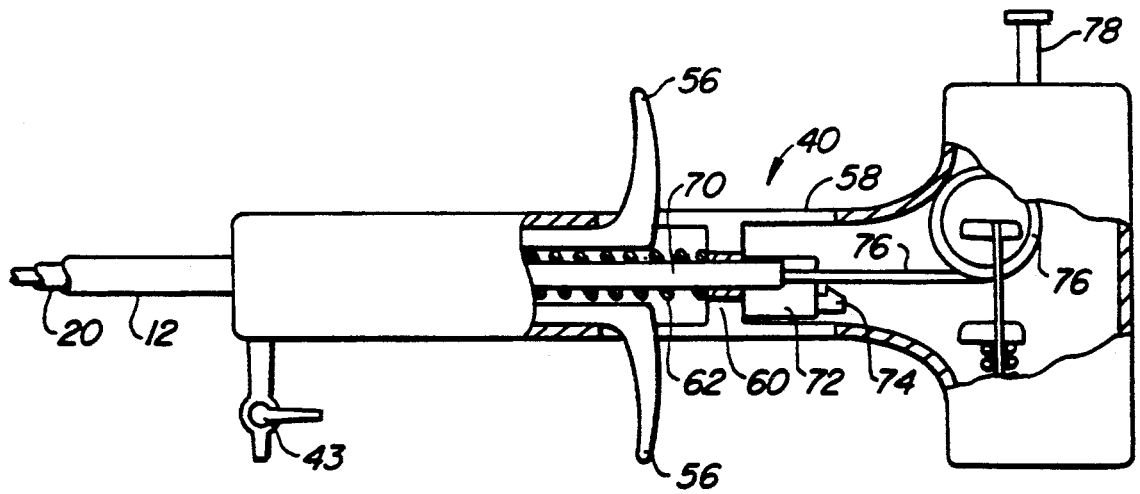
FIG. 6 is a detailed view of the proximal end of the device of FIG. 1, shown with portions broken away and the needle reciprocation mechanism in its extended configuration.

Referring now in particular to FIGS. 5 and 6, a housing or handle 40 is secured to the proximal end 14 of shaft 12. The housing 40 includes a socket or receptacle 42 which receives the shaft 12 and which is interconnected with a lateral passage 44 which receives the vacuum connector 45. The vacuum connector 45 is connected to the interior 28 of the shaft 12 through a port 46, and a vacuum can thus be selectively applied to the interior 28 by manipulating a valve, such as stopcock 43. In this way, the vacuum may be selectively applied to the vacuum ports 26 in the aperture 18.

Needle 22 passes from the shaft 12 and the needle tube 20 into interior 50 of the housing 40 through a vacuum-tight seal, such as O-ring 52. The needle 22, in turn, is connected to a T-slide member 54 which is reciprocatably mounted in the interior 50 of the housing 40. The T-slide 54 includes tabs 56 which extend laterally outward through slots 58 formed in the sides of housing 40. Thus, the T-slide 54 can be moved in the proximal direction to shift needle 22 from its extended configuration (FIG. 6) to its retracted configuration (FIG. 5) by the user pulling proximally on the tabs 56. The T-slide 56, and thus the needle 22, are returned to their extended configurations by a spring-loaded release mechanism, as will now be described.

A transverse member 60 is formed in the interior 50 of housing 40. A spring 62 extends between the transverse member 60 and an interior wall 64 formed near the distal end of the T-slide 54. In this way, the spring 62 is axially compressed as the T-slide 54 is pulled in the proximal direction. T-slide 54 and needle 22 can then be returned to their extended configuration by releasing the T-slide so that it is thrust forward by the action of spring 62.

The T-slide 54, however, is held in its retracted configuration (FIG. 5) by a latch mechanism which includes a tubular extension 70 (which is concentrically received within the interior of spring 62 and extends proximally from the T-slide 54). A block 72 having a hook 74 is attached to the proximal end of the tubular extension 70. A flexible fluid connection tube 76 is attached to the extension tube 70 and interconnected with the hollow interior of needle 22. Thus, the fluid to be delivered through needle 22 can be connected through a fixed port 78, with the flexible tube 76 providing the necessary slack to accommodate reciprocation of the tubular extension 70.

When the T-slide 54 is pulled fully in the proximal direction to retract needle 22, the hook 74 engages a stop plate 80 which extends between mounting studs 82 and 84 and is attached to a release button 86. The stop plate 80 is urged in the laterally outward direction (i.e., the downward direction in FIG. 5) by spring 88, and firmly engages the hook 74 while in this position. The hook 74, however, can be released by depressing release button 86, thus allowing spring 62 to thrust the T-slide 54 (and thus needle 22) in the forward or distal direction. This, of course, corresponds to a change in position of the distal end 24 of needle 22 between the retracted configuration (FIG. 3) and the extended configuration (FIG. 4).

Optionally, the extension tube 70 may be decoupled from the T-slide 54 so that the needle 22 may be released to advance forwardly while the T-slide 54 remains in place. Such a design is advantageous since it prevents the tabs 56 from shooting forward when the needle is actuated. Frequently, it will be desirable to also incorporate a safety latch or other mechanism which prevents accidental release of the needle 22.

While this particular embodiment of the housing 50 and needle release mechanism is felt to be an effective and reliable design for use in the present invention, it will be appreciated that numerous mechanisms can be devised for manipulating the needle between retracted and extended configurations. The present invention is in no way intended to be limited to this particular needle reciprocation and release mechanism and it is provided only as being exemplary of useful mechanisms.

Figure 7:
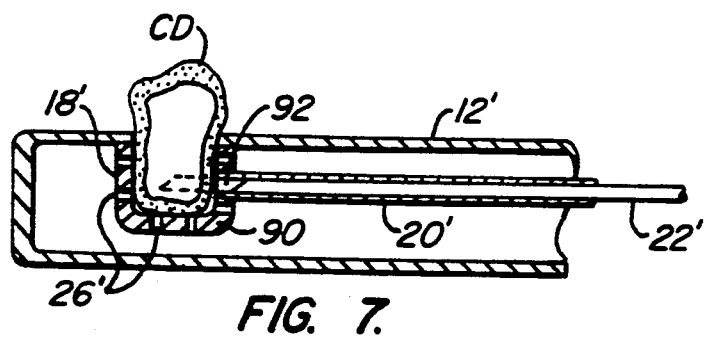
FIG. 7 illustrates a first alternative embodiment of a capture mechanism suitable for use in the devices of the present invention.

Referring now to FIG. 7, an alternate embodiment of the distal end of a shaft 12' having a laterally extending aperture 18' is illustrated. The aperture 18' is defined by separate U-shaped plate 90 having a plurality of vacuum ports 26' formed therein. Needle tube 20' is aligned with a port 92 formed in the side of U-shaped plate 90 and permits needle 22' to penetrate cystic duct CD held within the aperture 18'. The configuration of FIG. 7 allows the user to grab the cystic duct CD by a lateral movement of the shaft 12' rather than a distal thrust of the shaft 12 as required for the embodiment of FIGS. 1-6.

Figure 8:
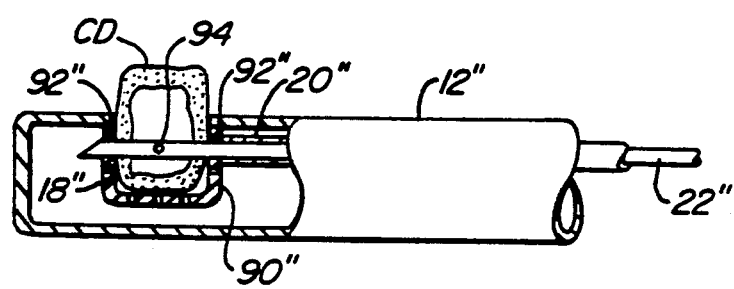
FIG. 8 illustrates a second alternative embodiment of a capture mechanism suitable for use in the devices of the present invention.

FIG. 8 illustrates a second alternative embodiment of the present invention. A shaft 12" includes a similar lateral aperture 18" formed by a U-shaped plate 90". The needle tube 20" is secured to one side of the U-shaped plate 90". Instead of a single aperture in the U-shaped plate, however, a pair of aligned apertures 92" are provided so that the needle 22" can extend between opposed wall surfaces of the cystic duct CD held in aperture 18". A perfusion port 94 is provided in the side of needle 22" to permit the fluid contrast media to be introduced into the lumen of the cystic duct CD while the needle is fully extended. The distal tip of the needle 22" will be sealed so that fluid is not leaked into the interior of the shaft 12".

Figure 9:
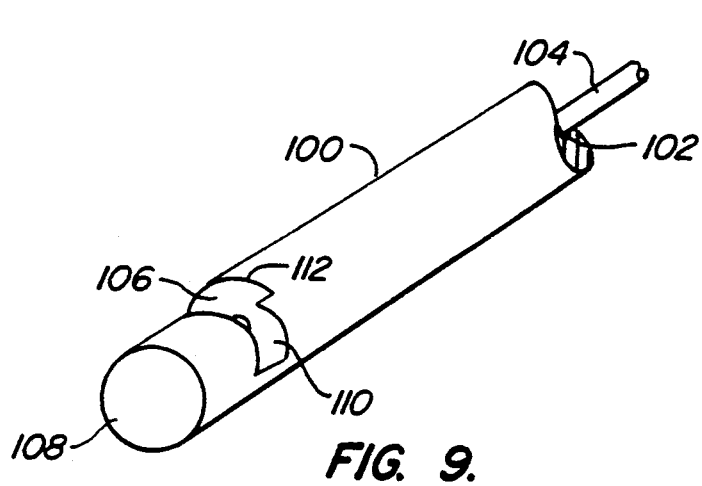
FIGS. 9 and 10 illustrate a third alternative embodiment of a capture mechanism suitable for use in the devices of the present invention.
Figure 10:
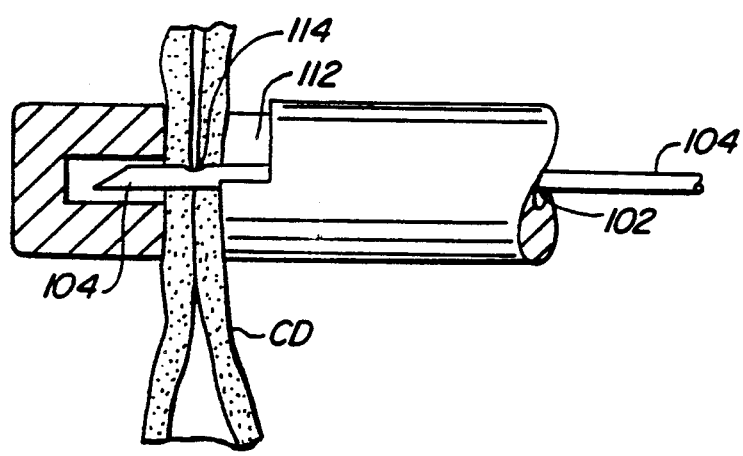

A third embodiment of the distal end of a shaft 100 useful as the device of the present invention is illustrated in FIGS. 9 and 10. The shaft 100 includes a single narrow-diameter lumen 102 carrying a needle 104. A slot 106 is formed near the distal end 108 of the shaft 100 and includes a narrow portion 110 and a wider portion 112. As best observed in FIG. 10, a cystic duct CD can be captured in the slot 106, with the narrow portion 110 holding the lumen of the cystic duct CD essentially closed. By then inserting the needle 104 through the collapsed walls of the cystic duct CD (using a mechanism which is not illustrated but which would be similar to that described in FIGS. 5 and 6), a perfusion port 114 can be aligned with the lumen portion of the cystic duct CD which is in the wider half 112 of the slot 106. It will be appreciated that the lumen gradually opens in the direction in which the perfusion port 114 is oriented. Thus, fluid which is introduced through the needle 104 can enter the lumen of the cystic duct CD through the perfusion port 114. This embodiment does not require vacuum ports in order to retain the cystic duct CD in the slot 106. Optionally, the slot 106 could be provided with movable jaws or clamps to help capture and subsequently tighten and seal the lumen of the cystic duct CD in the narrow portion 110 of the slot 106.

Figure 11:
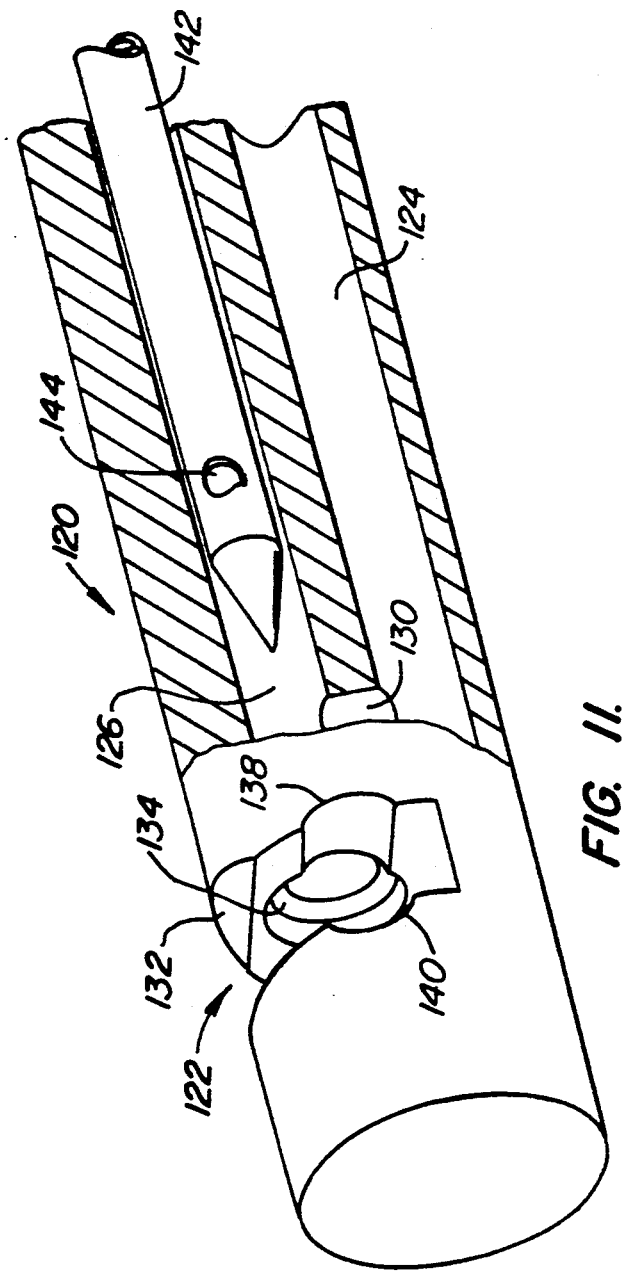
Figure 13:
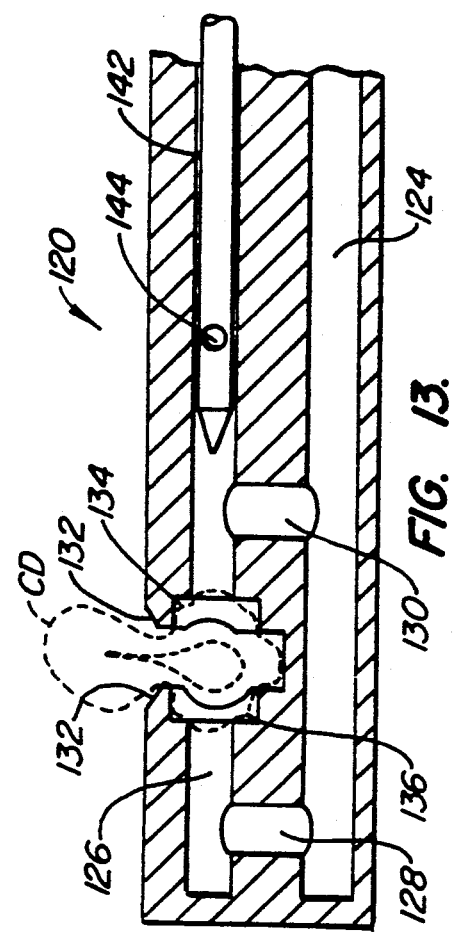
Figure 12:
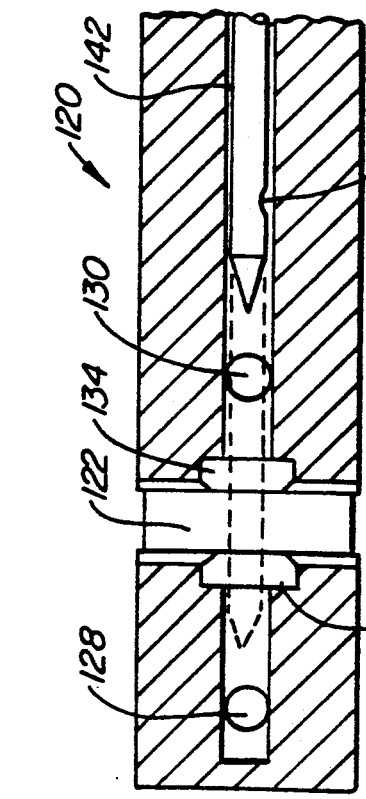

Referring now to FIGS. 11-13, yet another alternate embodiment of a shaft 120 having a laterally extending aperture 122 is illustrated. The shaft 120 includes a pair of parallel, axial passages 124 and 126 which are interconnected near the distal end of the shaft by lateral passages 128 and 130. The lateral passages 128 and 130 are formed on opposite sides of the aperture 122, for reasons that will be described below.

The aperture 122 includes beveled surfaces 132 near its entrance to facilitate capture of the cystic duct CD, as illustrated in broken line in FIG. 13. The aperture 122 further includes expanded regions 134 and 136 which act as transitions between axial passage 126 and the interior of the aperture 122. Finally, the aperture 122 includes a pair of lateral detents 138 and 140 which assist in holding the cystic duct CD or other body structure in place in the aperture.

The axial passage 126 provides the necessary conduit for fluid delivery needle 142. The needle 142, as in previous embodiments, may be advanced from a retracted position (as shown in full line in FIGS. 11-13) and an extended position (as shown in broken line in FIG. 12). In the extended position, a perfusion port 144 will be located generally in the middle of aperture 122 to permit delivery of the contrast media into the cystic duct CD. The needle 142 and shaft 120 may be connected to a suitable proximal housing, generally similar to that illustrated in FIGS. 5 and 6.

In use, the shaft 120 will be manipulated to capture the cystic duct CD so that the length of the duct is oriented laterally within the aperture 122. After the cystic duct CD is in place, a vacuum will be applied through axial passage 124, causing reduced pressure on either side of the aperture 122. That is, pressure in the regions of axial passage 126 on either side of the aperture 122 will be lowered by communication through lateral passages 128 and 130. Such reduced pressure will cause the exterior of the cystic duct CD to be drawn into regions 134 and 136 of the aperture 122, eventually being pulled into the two ports opening into axial passage 126. Continued application of a vacuum through passage 124 will enhance the seal between the axial passage 126 and the cystic duct CD.

After the cystic duct CD is in place and the seal has been effected by application of a vaccum, the needle 142 may be advanced forward so that it penetrates through both sides of the cystic duct CD. The perfusion port 140 on needle 142 will then lie within the interior lumen of the cystic duct CD and a suitable contrast media or other fluid can be introduced. By continuing to apply the vacuum through axial passage 124, the cystic duct CD will remain sealed to the axial passage 126, thus inhibiting loss of the fluid being introduced from the cystic duct CD and the device.

Although the foregoing invention has been described in detail for purposes of clarity of understanding, it will be obvious that certain modifications may be practiced within the scope of the appended claims.

What is claimed is:

1. A device for introducing a fluid into a lumen of a body duct, said device comprising:

a shaft having a proximal end and a distal end;
   means at the distal end of the shaft for capturing the duct;
   a needle disposed within the shaft;
   means at the proximal end of the shaft for advancing the needle to pierce a duct held within the capturing means; and
   means for introducing the fluid through the needle and into the lumen of the duct.

2. A device as in claim 1, wherein the means for capturing the duct comprises an aperture formed in the shaft.

3. A device as in claim 2, wherein the aperture includes means for applying a vacuum to the body duct to hold the lumen open.

4. A device as in claim 1, wherein the means for advancing the needle includes a spring secured between the shaft and the needle, and a release mechanism which holds the needle in a retracted position with the spring deformed and selectively releases the needle to move under the force of the spring to pierce the duct.

5. A device for introducing a fluid into a lumen of a body duct, said device comprising:

a shaft having a proximal end, a distal end, and an axial passage therethrough;
   a slot formed in the distal end of the shaft for capturing and maintaining the duct in an orientation generally transverse to the axial passage;

a hollow needle disposed within the axial passage of the shaft and having at least one perfusion port near its distal end;

means at the proximal end of the shaft for advancing the needle to pierce a duct held within the slot so that the perfusion port is within the lumen; and means for introducing the fluid through the perfusion port and into the lumen of the duct.

6. A device as in claim 5, further comprising vacuum ports formed over a surface of the slot and means for connecting the ports to an external vacuum source.

7. A device as in claim 5, further comprising means for applying a vacuum in the axial passage so that the body duct can be drawn into and sealed against the passage to inhibit leakage of the fluid.

8. A device as in claim 5, wherein the means for advancing the needle causes the needle to pierce one wall with the distal tip of the needle remaining in the lumen of the duct.

9. A device as in claim 5, wherein the means for advancing the needle causes the needle to pierce opposed walls of the duct.

10. A device as in claim 8, wherein the perfusion port is open forwardly at the distal tip of the needle.

11. A device as in claim 9, wherein the perfusion port is open laterally and spaced rearwardly from the distal tip of the needle.

12. A device as in claim 5, wherein the means for advancing the needle includes a spring secured between the shaft and the needle, and a release mechanism which holds the needle in a retracted position with the spring deformed and selectively releases the needle to move under the force of the spring to pierce the duct.

13. A method for introducing a fluid into a lumen of a body duct, said method comprising:

capturing the body duct with the distal end of a shaft;

piercing a needle reciprocatably attached to the shaft through a wall surface of the body duct while said wall surface is held by the shaft; and introducing the fluid through the needle into the lumen.

14. A method for introducing a fluid into a lumen of a body duct, said method comprising:

percutaneously introducing a shaft so that a distal end of the shaft lies proximate the body duct;

manipulating a proximal end of the shaft so that the distal end captures the body duct;

manipulating a needle from the proximal end of the shaft so that the needle pierces a portion of the duct captured by the shaft; and introducing fluid through the needle into the shaft.

15. A method as in claim 14, wherein the body duct is the cystic duct and the fluid is contrast medium.

16. A method as in claim 15, wherein the shaft is introduced through a cannula and manipulated while viewed through a laparoscope.

17. A method as in claim 14, further comprising applying a vacuum through the distal end of the shaft to hold the body duct.

18. A method as in claim 17, wherein the vacuum is applied to opposed sides of the body duct to hold the lumen open.

19. A method as in claim 14, wherein the needle is manipulated to deform a spring and then released to allow the needle to spring forward and pierce the body duct.

20. A method as in claim 14, wherein the needle pierces one wall surface of the duct and the fluid is introduced through a perfusion port at the distal tip of the needle.

21. A method as in claim 14, wherein the needle pierces opposed surfaces of the duct and the fluid is introduced through a perfusion port open laterally on a side of the needle spaced proximally from the distal tip.

* * * * *